United States Patent [19]

Bulten et al.

[11] Patent Number: 4,482,569

[45] Date of Patent: * Nov. 13, 1984

[54] PLATINUM (IV)-DIAMINE COMPLEXES, A PROCESS FOR THE PREPARATION OF PHARMACEUTICAL COMPOSITIONS AND A METHOD OF TREATING MALIGNANT TUMORS IN MICE

[75] Inventors: Eric J. Bulten, Bilthoven; Francois Verbeek, Harmelen, both of Netherlands

[73] Assignee: Nederlandse Centrale Organisatie Voor Toegepastnatuurweten-Schappelijk Onderzoek, The Hague, Netherlands

[*] Notice: The portion of the term of this patent subsequent to Feb. 14, 2001 has been disclaimed.

[21] Appl. No.: 458,979

[22] Filed: Jan. 18, 1983

Related U.S. Application Data

[63] Continuation-in-part of Ser. No. 232,298, Feb. 6, 1981.

[30] Foreign Application Priority Data

Jan. 3, 1980 [NL] Netherlands .................. 8000032
Dec. 30, 1980 [JP] Japan ..................... 55-189451

[51] Int. Cl.³ .................. A01N 55/02; A61K 31/28; C07F 15/00
[52] U.S. Cl. .................. 424/287; 260/429 R
[58] Field of Search .................. 260/429 R; 424/287

[56] References Cited

U.S. PATENT DOCUMENTS

| | | |
|---|---|---|
| 4,053,587 | 10/1977 | Davidson et al. |
| 4,119,654 | 10/1978 | Tobe et al. |
| 4,140,707 | 2/1979 | Cleare et al. |
| 4,228,090 | 10/1980 | Hydes et al. |
| 4,250,189 | 2/1981 | Hydes et al. |
| 4,255,347 | 3/1981 | Kidani et al. ............... 260/429 R |

OTHER PUBLICATIONS

Chemical Abstracts, 77, 169424s, (1972).
B. Rosenberg and L. Van Camp, Cancer Research 30, (1970), 1799-1802.
A. P. Zipp and S. G. Zipp, J. Chem. Ed., 54 (12), (1977), p. 739.
Chem. and Eng. News, Jun. 6, 1977, pp. 29-30.
Cancer Chemotherapy Reports Part 1, vol. 59, No. 3, May/Jun. 1975, pp. 629-641.
M. L. Tobe and A. R. Khokhar, J. Clinical Hematol. Oncol., 7 (1), (1977), pp. 114-134.
Appleton, T. C. and Hall, J. R., Inorganic Chemistry, vol. 11, No. 1, 1972, pp. 112-117.
Braddock et al., Chemico-Biological Interactions, vol. 11, No. 3, pp. 158-159, (1975).

*Primary Examiner*—Helen M. S. Sneed
*Attorney, Agent, or Firm*—Brumbaugh, Graves, Donohue & Raymond

[57] ABSTRACT

This invention relates to novel-platinum (IV)-diamine complexes, a pharmaceutical composition using the novel complexes and methods of treating malignant tumors in mice using the pharmaceutical composition.

9 Claims, No Drawings

PLATINUM (IV)-DIAMINE COMPLEXES, A PROCESS FOR THE PREPARATION OF PHARMACEUTICAL COMPOSITIONS AND A METHOD OF TREATING MALIGNANT TUMORS IN MICE

BACKGROUND OF THE INVENTION

This application is a continuation-in-part of U.S. patent application Ser. No. 232,298 filed Feb. 6, 1981.

The invention relates to new platinum (IV)-diamine complexes, a process for the preparation of pharmaceutical compositions using the platinum (IV)-diamine complexes and a method for the treatment of malignant tumors in mice.

From the literature it is known that platinum-diamine complexes, derived from bivalent platinum as well as from tetravalent platinum are usable for the treatment of cancer, for example, the article of B. Rosenberg and L. van Camp, Cancer Research 30 (1970) 1799–1802.

The article by A. P. Zipp and S. G. Zipp, J. Chem. Ed., 54 (12) (1977), page 739, which describes the use of cis-platinum diamine dichloride for the treatment of cancer is relevant with respect to the use of bivalent platinum-diamine complexes, like the cis-platinum diamine dichloride, for the treatment of cancer. Platinum compounds have a broad spectrum as antitumor agents, but also have significant side effects, especially kidney toxicity. As a method for counteracting kidney toxicity a combination of the cis-platinum diamine dichloride with another substance or with the use of large amounts of liquid or other techniques to flush the kidneys have been proposed.

J. Clinical Hematol, Oncol., 7 (1) (1977), pages 114–134, mentions a large number of platinum-diamine complexes, such as cis-platinum-dichloro diamine for the treatment of cancer. This article also mentions kidney toxicity as the most important side effect of the compounds.

Chem. and Eng. News, June 6, 1977, pages 29–30, describes the cis-platinum diamine dichloride compound and the use thereof for the treatment of cancer. This article also mentions kidney toxicity as the most important disadvantage of that compound.

An article in Cancer Chemotherapy Reports Part 1, Vol. 59, No. 3, May/June 1975, pages 629–641 also mentions the kidney toxicity of cis-dichloro diamine platinum (II). Because of this kidney toxicity and the low therapeutic index of cis-platinum dichloride other platinum complexes were investigated for the treatment of cancer.

In Dutch patent applications 78.07334 and 79.04740 new platinum (II)-diamine complexes are described, which are well suited for the treatment of cancer and which exhibit low or no kidney toxicity. These applications use so-called bidentate ligand complexes from bivalent platinum, characterized by the formula:

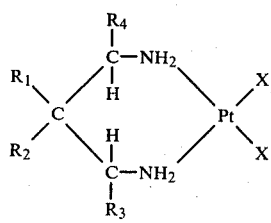

(1)

wherein the bidentate ligand is a substituted or unsubstituted propane diamine. These compounds exhibit, low or no kidney toxicity because of the nature of the substituents $R_1$, $R_2$, $R_3$ and $R_4$.

The above-mentioned article from Rosenberg and Van Camp describes for the first time the antitumor activity of tetravalent platinum (IV) diamine complexes, i.e., the cis-platinum (IV) diamine tetrachloride, having the formula:

(2)

This compound is also discussed by M. L. Tobe and A. R. Khokhar, J. Clinical Hematol. Oncol., 7 (1) (1977), pages 114–134, together with a large number of other platinum (IV) complexes having two primary amines as monodentate ligands with the formula:

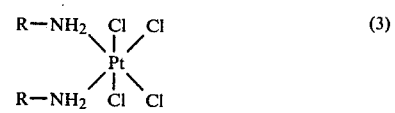

(3)

Similar complexes are also described in Dutch patent application 78.10431, which also relates to monodentate ligand complexes, characterized by formula 3, wherein R has the general formula cyclo-$C_nZ_{2n-1}$.

Platinum (IV) complexes with bidentate amine ligands, wherein the amine groups are separated from each other by two carbon atoms (ethylene group), having formula 4:

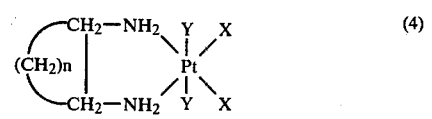

(4)

are mentioned in J. Clinical Hematol. Oncol., 7 (1) (1977), pages 231–241, and in Dutch patent application 79.03048. Platinum (IV) complexes with bidentate amino acid ligands, wherein the platinum is partly complexed with nitrogen and partly with oxygen groups, are described in Dutch patent application 79.03050.

The present invention relates to a series of new platinum (IV)-diamine complexes, which are characterized by the general formula:

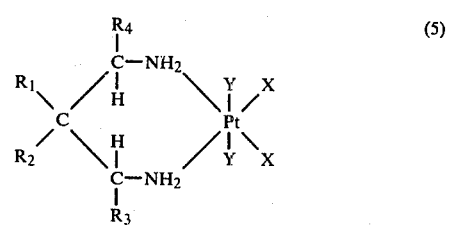

(5)

wherein $R_1$ and $R_2$ independently from each other are a hydrogen atom or a substituted or unsubstituted alkyl group having 1–20 carbon atoms, a cycloalkyl group having 3–7 carbon atoms, an aryl or aralkyl group having 1–20 carbon atoms in the alkyl group, whereas $R_1$ and $R_2$ together may be a substituted or unsubstituted cycloalkyl group having 3–7 carbon atoms, $R_3$ and $R_4$ are independently from each other a hydrogen atom or a substituted or unsubstituted alkyl group having 1–20 carbon atoms, or an aryl or aralkyl group having 1–20 carbon atoms in the alkyl group, and X and Y are the same or different anionic groups.

Based on the high anti-tumor activity and the low kidney toxicity of compounds having formula 6:

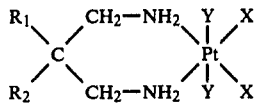  (6)

wherein $R_1$, $R_2$, X and Y have the above meaning. Compounds wherein at least one or both group $R_1$ or $R_2$ have more than one carbon atom, are preferred.

Preferably compounds having the following formulae and most preferably the cis-dichloro-trans-dihydroxy-1,1-bis(aminomethyl)cyclohexane platinum (IV) (formula 7) and the cis-tetrachloro-1,1-bis(aminomethyl)-cyclohexane platinum (IV) (formula 8) are used:

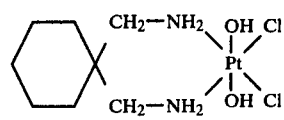  (7)

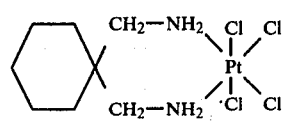  (8)

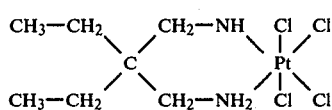  (9)

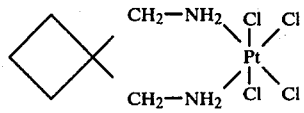  (10)

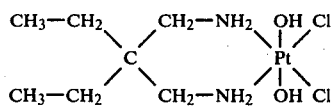  (11)

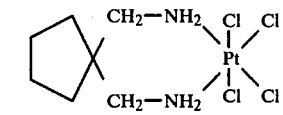  (12)

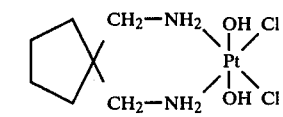  (13)

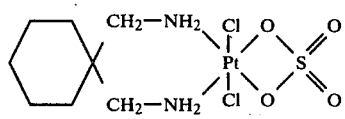  (14)

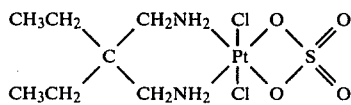  (15)

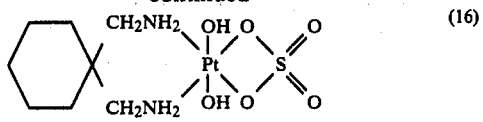  (16)

In formulae 5 and 6, the anionic group X is preferably chlorine, bromine or iodine, a substituted or unsubstituted carboxylate radical, like an acetate or a substituted acetate. The two X's together can also be a suphate radical, an oxalate, malonate or substituted malonate group or a 4-carboxyphthalate group. The anionic group Y is (independently from X) preferably chlorine, bromine or iodine, a hydroxyl group or a nitrate group.

Extensive investigation has proved that the compounds according to the invention exhibit a high therapeutic activity against malignant tumors in mice. The results of this investigation are set forth in Table A.

TABLE A

Anti-tumor Activity in BDF-1 Mice[a]

| Compound | Tumor | Dose/injection (mg/kg) | T/C[e] (%) |
|---|---|---|---|
| cis-DDP[b] | LE[c] | 10 | 186 |
| Formula 7 | " | 16 | 214 |
| Formula 7 | " | 12 | 283 |
| Formula 8 | " | 12 | 236 |
| Formula 9 | " | 8 | 229 |
| Formula 10 | " | 8 | 207 |
| Formula 12 | " | 6 | 257 |
| Formula 14 | " | 6 | 233 |
| Formula 15 | " | 12 | 225 |
| Formula 16 | " | 21 | 183 |
| cis-DDP | LE/cis DDP[d] | 8 | 121 |
| Formula 7 | " | 15 | 229 |
| Formula 8 | " | 6 | 171 |
| Formula 12 | " | 4 | 138 |
| Formula 14 | " | 6 | 436[f] |
| Formula 15 | " | 4 | 188[g] |
| Formula 16 | " | 7 | 150[h] |

[a] For detailed information concerning the test procedure and its interpretation, see Introduction 14, Screening data summary interpretation, and outline of current screen, Drug Evaluation Branch, National Cancer Institute, Bethesda, Maryland 20014, 1977.
[b] Cis-diaminedichloroplatinum(II)
[c] LE = L-1210 lymphoid leukemia
[d] A subline of L-1210 resistant to cis-DDP
[e] Period of survival of the mice treated (T) in relation to untreated mice (C); the therapeutic activity is significant at T/C 125.
[f] 4 out of 6 mice cured
[g] 1 out of 6 mice cured
[h] 3 out of 6 mice cured Contrary to the results for known platinum complexes used for the treatment of cancer, such as the cis-platinum diamine chloride (DDP), it appears from the results set forth in Table B below that the compounds according to the claimed invention show low or no kidney toxicity.

TABLE B

Percentage of Blood Urea-Nitrogen (BUN) After Administering Platinum Complexes (in the Rat)[a]

| Compound | Dose (mg/kg) | Incidence of BUN 30 mg % |
|---|---|---|
| Cis-DDP | 18 | 8/10 |
|  | 13 | 9/10 |
| Formula 7 | 29 | 0/10 |
|  | 16 | 0/10 |
| Formula 8 | 16 | 0/10 |
|  | 9 | 0/10 |
| Formula 9 | 27 | 1/9 |
|  | 15 | 0/10 |
| Formula 10 | 11 | 0/10 |
|  | 6 | 0/10 |
| Formula 12 | 11 | 1/10 |

TABLE B-continued

Percentage of Blood Urea-Nitrogen (BUN) After Administering Platinum Complexes (in the Rat)[a]

| Compound | Dose (mg/kg) | Incidence of BUN 30 mg % |
|---|---|---|
| | 6 | 0/10 |

[a] A generally acknowledged significant method for determination of kidney toxicity concerns the evaluation of the blood urea-nitrogen; BUN values ≧30 mg % are considered indicative of drug-induced nephrotoxicity.

The invention is further illustrated by the following examples.

Preparation of the platinum complexes

The complexes are prepared by a general process, wherein first the platinum (II) product is prepared and is then converted by means of an oxidation agent to the corresponding platinum (IV) compound.

The platinum (II) product with the general formula cis-LPtCl$_2$, wherein L is the diamine (bidentate ligand) in the complex, is prepared according to the method of: G. L. Johnson, Inorg. Synth. VIII, 242–244.

From the desired diamine first the di-HCl-salt is prepared. This is dissolved in water, thereafter the equimolecular amount of K$_2$PtCl$_4$ is added. The mixture is then heated to 95° C. Now an equimolecular amount of NaOH in water is added so quickly that the pH remains at about 6. The light yellow precipitate which forms is filtered, washed with water and dried. The product obtained can be purified by recrystallization from DMF.

The cis-LPtCl$_2$ (II) is converted with chlorine gas to cis-LPtCl$_4$-IV and with hydrogen peroxide (30%) it is oxidized to cis-LPt-(OH)$_2$Cl$_2$ (IV).

The conversion to cis-LPtCl$_4$ (IV) is described in Inorg. Synth. VII, 236–238, by G. B. Kaufman.

The cis-LPtCl$_2$ is suspended in water and oxidized by passing through at 70°–75° C. chlorine gas for about one hour. Thereafter, air is sucked through to remove the excess chlorine (temperature=70° C., time: 5 minutes). The mixture is cooled, the product is filtered, washed with water and dried under reduced pressure.

The oxidation to cis-LPt(OH)$_2$Cl$_2$ (IV) takes place by boiling a suspension of cis-LPtCl$_2$ (II) for 0.5 hour with an excess of 30% H$_2$O$_2$. The suspension is cooled and the product is filtered, washed with water and dried under reduced pressure.

The conversion of the cis-LPt(OH)$_2$Cl$_2$ (IV) to cis-LPt-Cl$_4$ (IV) may also be carried out by heating a suspension of the cis-LPt (OH)$_2$Cl$_2$ (IV) for 5 minutes at 100° C. with concentrated hydrochloric acid.

The latter two reactions are described in J. Am. Chem. Soc., 72, 2433 (1950) by F. Basolo, J. C. Bailar Jr. and B. Rapp-Tarr, but are slightly modified by boiling the reaction product instead of heating at 80° C.; the use of 30% H$_2$O$_2$ instead of 10% H$_2$O$_2$; excess H$_2$O$_2$; 50–70 instead of 10.

EXAMPLE I

Cis-Dichloro-Trans-Dihydroxy-1,1-Bis(Aminomethyl)-Cyclohexane Platinum (IV) (Formula 7)

1.2 g cis-dichloro-1,1-bis(aminomethyl)-cyclohexane platinum (IV) is suspended in 5 ml distilled water. 25 ml 30% hydrogen peroxide is added. Stirring is carried out during 0.5 hours at room temperature, thereafter one hour under reflux. The suspension is cooled and the solid substance is filtered, washed with water and dried under reduced pressure. Weight or light yellow solid substance: 0.45 g Analysis (weight%): Calculated: C 21.73; H 4.56; H 6.33; Pt 44.11; Cl 16.03; Found: C 21.78; H 4.54; H 6.21; Pt 43.98; Cl 15.85

IR-spectrum(CsI-pill): Pt-Cl 332 cm$^{-1}$ Pt-O 545 cm$^{-1}$

EXAMPLE II

Cis-Tetrachloro-1,1-Bis-(Aminomethyl)-Cyclohexane Platinum (IV) (Formula 8)

1.2 g cis-dichloro-1,1-bis(aminomethyl)cyclohexane platinum (II) is suspended in 15 ml distilled water. The suspension is then heated to 70° C., whereafter under stirring during one hour chlorine gas is introduced. The excess chlorine gas is removed by passing air through the reaction mixture (temperature=70° C.). The reaction mixture is cooled and the solid substance is filtered, washed with water and dried under reduced pressure.

Weight of yellow solid substance: 0.9 g (63%).

Analysis (weight %): Calculated: C 20.05; H 3.79; N 5.85; Pt 40.72; Found: C 20.20; H 3.74; N 5.88; Pt 40.90

'H-NMR spectrum in DMSO-d$_6$ (Varian-T 60)

| CH$_2$(ring) | 1.35 ppm | |
|---|---|---|
| CH$_2$(NH$_2$) | 2.23 ppm | |
| NH$_2$ | 6.30 ppm | with respect to TMS |
| | 6.80 ppm | |
| | 7.27 ppm | |

IR-spectrum (CsI-pill): Pt-Cl 332–350 cm$^{-1}$

EXAMPLE III

Cis-Tetrachloro-2,2-Diethyl-1,3-Diaminopropane Platinum (IV) (Formula 9)

This complex was prepared in the same way as in Example II starting from 1.6 g cis-dichloro-2,2-diethyl-1,3-diaminopropane platinum(II).

Yield: 1.5 g (79%)

Analysis (weight %): Calculated: C 18.00; H 3.88; N 6.00; Pt 41.76; Found: C 18.25; H 3.90; N 6.32; Pt 41.21

'H-NMR-spectrum in DMSO-d6 (Varian-T 60)

| CH$_3$(Et) | 0.73 ppm | |
|---|---|---|
| CH$_2$(Et) | 1.23 ppm | |
| CH$_2$(NH$_2$) | 2.20 ppm | |
| NH$_2$ | 6.18 ppm | with respect to TMS |
| | 6.70 ppm | |
| | 7.15 ppm | |

IR-spectrum (CsI-pill): Pt-Cl 343 cm$^{-1}$

EXAMPLE IV

Cis-Tetrachloro-1,1-Bis(Aminomethyl) Cyclobutane Platinum (IV) (Formula 10)

This product was prepared in the same way as in Example II. Starting from 1.14 g cis-dichloro-1,1-bis-(aminomethyl) cyclobutane platinum (II) 1.2 g (88%) of the desired product was isolated.

Analysis (weight %): Calculated: C 15.98; H 3.13; N 6.21; Pt 43.25; Found: C 16.06; H 3.07; N 6.23; Pt 43.35

'H-NMR-spectrum in DMSO-d6 (Varian T 60)

| CH$_2$ ring | 1.82 ppm | |
|---|---|---|
| CH$_2$(NH$_2$) | 2.40 ppm | |
| NH$_2$ | 6.30 ppm | with respect to TMS |
| | 6.78 ppm | |

7.30 ppm

IR-spectrum (CsI-pill): Pt-Cl: 350 cm$^{-1}$

EXAMPLE V

Cis-Dichloro-Trans-Dihydroxy-2,2-Diethyl-1,3-Diaminopropane Platinum (IV) (Formula 11)

This complex was prepared in the same way as in Example I starting from 1.5 g cis-dichloro-2,2-diethyl-1,3-diaminopropane platinum(II).

Yield: 0.95 g (58%)

Analysis (weight %): Calculated: C 19.54; H 4.69; N 6.51; Pt 45.34; Cl 16.48; Found: C 19.62; H 4.8; N 6.3; Pt 45.5; Cl 16.4

IR-spectrum (CsI-pill): Pt-Cl: 343 cm$^{-1}$
Pt-O: 542 cm$^{-1}$

EXAMPLE VI

Cis-Tetrachloro-1,1-Bis-(Aminomethyl)Cyclohexane Platinum (IV) (Formula 8)

Cis-dichloro-trans-dihydroxy-1,1-bis(aminomethyl) cyclohexane platinum (IV) was prepared as in Example I, whereafter hydrochloric acid was added to the obtained suspension. After heating for 5 minutes at 95°–100° C. the reaction mixture was cooled. The product was filtered and washed with water.

The compound was characterized in that the 'H-NMR- as well as the IR-spectrum appeared to be identical to the spectra of Example II.

EXAMPLE VII

Cis-Tetrachloro-1,1-Bis-(Aminomethyl) Cyclopentane Platinum (IV) (Formula 12)

This complex was prepared in the same way as in Example II, starting from 1.6 g cis-dichloro-1,1-bis-(aminomethyl) cyclopentane platinum (II).

Yield: 1.3 g (69%)

Analysis (weight%): Calculated: C 18.08; H 3.47; N 6.02; Pt 41.94; Found: C 18.20; H 3.48; N 6.09; Pt 42.11

'H-NMR spectrum in DMSO-d6 (Varian-T 60)

| CH$_2$ (ring) | 1.50 ppm | |
|---|---|---|
| CH$_2$ (NH$_2$) | 2.23 ppm | |
| NH$_2$ | 6.33 ppm | with respect to TMS |
| | 6.80 ppm | |
| | 7.20 ppm | |

IR-spectrum (CsI-pill): Pt-Cl 342 cm$^{-1}$

EXAMPLE VIII

Cis-Dichloro-Trans-Dihydroxy-1,1-Bis-(Aminomethyl) Cyclopentane Platinum (IV) (Formula 13)

This complex was prepared in the same way as in Example I starting from 1.2 g cis-dichloro-1,1-bis-(aminomethyl) cyclopentane platinum (II).

Yield: 0.6 g (47%)

Analysis: (weight %): Calculated: C 19.63; H 4.24; N 6.54; Pt 45.56; Cl 16.56; Found: C 19.54; H 4.11; N 6.66; Pt 45.47; Cl 16.49

IR-spectrum (CsI-pill): Pt-Cl 330–345 cm$^{-1}$; Pt-O 540 cm$^{-1}$

EXAMPLE IX

Cis-Sulfato-Trans-Dichloro-1,1-Bis-(Aminomethyl)Cyclohexane Platinum (IV) (Formula 14)

1 g. tetrachloro-1,1-bis-(aminomethyl)-cyclohexane platinum (IV) is suspended in 40 ml of distilled water. To this 0.62 g Ag$_2$SO$_4$ is added and the mixture is heated during 8 hours at 50°–55° C. while excluding light. After cooling the formed silver chloride is filtered off and the product is washed with distilled water (25 ml). The clear filtrate is concentrated under reduced pressure.

Weight of yellow solid: 0.9 g (85%)

IR spectrum (in KBr): S=O 1130 cm$^{-1}$ (v.s.); Pt=O 585 cm$^{-1}$ (s)

Analysis (weight %): Calc.+3H$_2$O: C 17.21; H 4.33; N 5.02; O 20.06; S 5.74; Found: C 17.3; H 4.1; N 5.1; O 20.1; S 5.5

'H-NMR spectrum in DMSO-d6 (VARIAN T-60) with respect to TMS

CH$_2$ (ring): 1.4 ppm
CH$_2$ (NH$_2$): 2.2 ppm
NH$_2$: 7.4 ppm

EXAMPLE X

Cis-Sulfato-Trans-Dichloro-2,2-Diethyl-1,3-Diaminopropaneplatinum (IV) (Formula 15)

1.4 g tetrachloro-2,2-diethyl-1,3-diaminopropaneplatinum (IV) is suspended in 30 ml distilled water. To this 0.9 g Ag$_2$SO$_4$ is added. During 22 hours the mixture is stirred at room temperature while excluding light. The silver chloride which forms is filtered off and the product is washed with distilled water (25 ml). Vaporizing the clear filtrate under reduced pressure yields 1.2 g of the desired product.

IR. spectrum (in KBr): Pt-O 585 cm$^{-1}$

Analysis (weight %): Calc.+2H$_2$O: C 15.91; H 4.20; N 5.30; Pt 36.93; Found: C 15.9; H 4.5; N 5.3; Pt 36.7

'H-NMR spectrum in D$_2$O (VARIAN T-60) with respect to trimethylsilyl propanesulfonic acid sodium salt CH$_3$ (ethyl): 0.85 ppm
CH$_2$ (ethyl): 1.37 ppm
CH$_2$ (NH$_2$): 1.9–2.9 ppm
H$_2$O (D$_2$O): 4.75 ppm

EXAMPLE XI

Cis-Sulfato-Trans-Dihydroxy-1,1-Bis-(Aminomethyl)-Cyclohexane Platinum (IV) (Formula 16)

1.3 g. cis-dichloro-transdihydroxy-1,1-bis-(aminomethyl) cyclohexane platinum (IV) is suspended in 40 ml distilled water. To this is added 0.9 Ag$_2$SO$_4$. The mixture is heated during 5 hours at 60° C. followed by 7 hours at 100°–110° C. while excluding light. The silver chloride which forms is filtered off and the product is washed with distilled water (20 ml). The clear filtrate is concentrated under reduced pressure.

Weight of yellow solid: 0.9 (65%).

IR spectrum (in KBr): S=O 1120 cm$^{-1}$ (v.s.); Pt=O 618 cm$^{-1}$ (s)

Analysis (weight %): Calc.: C 20.56; H 4.31; N 5.99; O 20.54; S 6.86; Found: C 20.3; H 4.2; N 5.9; O 20.6; S 6.9

'H-NMR spectrum in D$_2$O (VARIAN T-60) with respect to trimethylsilyl propanesulfonic acid sodium salt CH$_2$ (ring): 1.43 ppm (broad)

$CH_2(NH_2)$: 2.47 ppm (broad)

$OH-H_2O/D_2O$: 4.73 ppm

We claim:

1. Cis-sulfato-trans-dichloro-1,1-bis(aminomethyl)-cyclohexane-platinum(IV) having the formula:

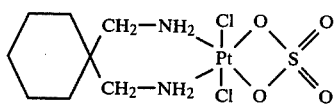

2. Cis-sulfato-trans-dichloro-2,2-diethyl-1,3-diamino-propaneplatinum (IV) having the formula:

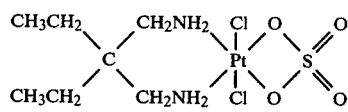

3. Cis-sulfato-trans-dihydroxy-1,1-bis(aminomethyl) cyclohexane-platinum (IV) having the formula:

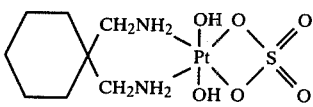

4. A pharmaceutical composition comprising a suitable carrier and an amount of the compound described in claim 1 sufficient to treat malignant tumors in mice.

5. A pharmaceutical composition comprising a suitable carrier and an amount of the compound described in claim 2 sufficient to treat malignant tumors in mice.

6. A pharmaceutical composition comprising a suitable carrier and an amount of the compound described in claim 3, sufficient to treat malignant tumors in mice.

7. A method of treating malignant tumors in mice which consists of administering a therapeutically effective amount of the composition as described in claim 4 to mice having malignant tumors.

8. A method of treating malignant tumors in mice which consists of administering a therapeutically effective amount of the composition as described in claim 5 to mice having malignant tumors.

9. A method of treating malignant tumors in mice which consists of administering a therapeutically effective amount of the composition as described in claim 5 to mice having malignant tumors.

* * * * *